United States Patent [19]

Yokota et al.

[11] Patent Number: 4,917,783
[45] Date of Patent: Apr. 17, 1990

[54] METHOD FOR PURIFYING MACROCYCLIC KETONES

[75] Inventors: Tadafumi Yokota; Hiroshi Okino, both of Saitama, Japan

[73] Assignee: Nippon Mining Co., Ltd., Tokyo, Japan

[21] Appl. No.: 176,054

[22] Filed: Mar. 31, 1988

[30] Foreign Application Priority Data

Mar. 31, 1987 [JP] Japan ................... 62-75914

[51] Int. Cl.$^4$ ............................. C07C 45/00
[52] U.S. Cl. .................. 204/157.15; 568/347
[58] Field of Search .............. 568/347; 204/157.15

[56] References Cited

U.S. PATENT DOCUMENTS 3,935,270 1/1976 Calderon ........................... 549/545
3,975,442 8/1976 Hajos ................................ 568/379

FOREIGN PATENT DOCUMENTS 46-37584 11/1971 Japan.
61-56145 3/1986 Japan.
61-56146 3/1986 Japan.
61-56147 3/1986 Japan.
61-56148 3/1986 Japan.
62-190140 8/1987 Japan.

Primary Examiner—John F. Niebling
Assistant Examiner—Isabelle Rodriguez
Attorney, Agent, or Firm—Sughrue, Mion, Zinn, Macpeak & Seas

[57] ABSTRACT

A method for purifying a macrocyclic ketone is disclosed which comprises light-irradiating a macrocyclic ketone containing a macrocyclic diketone as an impurity. Preferably, the macrocyclic ketone as light-irradiated is treated with an active charcoal so as to elevate the purity of the resulting macrocyclic ketone. For light-irradiation, the macrocyclic ketone may be in the form of an alcohol solution.

6 Claims, 1 Drawing Sheet

METHOD FOR PURIFYING MACROCYCLIC KETONES

FIELD OF THE INVENTION

The present invention relates to a method for purifying macrocyclic ketones and, more particularly, those having from 9 to 18 carbon atoms.

BACKGROUND OF THE INVENTION

Macrocyclic ketones having from 9 to 18 carbon atoms are useful as intermediates for medicines as well as perfumes or bases for perfumes.

For preparation of macrocyclic ketones, a method of cyclizing a diester of a linear alkanedicarboxylic acid by acyloin condensation reaction followed by reducing the thus cyclized intermediate has been proposed (*Helv. Chem. Acta.*, 30, 1741 (1947)). The macrocyclic ketones obtained by the said method as a final reaction product are colored in yellow and have a weak irritant odor as these are, and therefore the musky smell is weak as being effaced by the said bad odor and these could not satisfy the quality required of perfumes, etc. Accordingly, the macrocyclic ketones were hitherto purified by distillation under reduced pressure and recrystallization (V.V. Dhekne et al., *Indian J. Chem.*, 4, 524).

However, in order to improve the property of the macrocyclic ketones to such a degree that the ketones may be free from the coloration and bad odor for practical use by the purification process comprising the repetition of the above-mentioned distillation under reduced pressure and recrystallization, the number of the times of the repetition of the distillation and recrystallization is required to be increased, and as a result, the operation is complicated and the yield is poor. Thus the process is economically problematic.

SUMMARY OF THE INVENTION

The present inventors earnestly studied so as to overcome the above-mentioned problems and as a result have found that the coloration and bad odor result from a slight amount of macrocyclic diketones contained in the macrocyclic ketones; and the diketones can more easily be decomposed or polymerized under light than the ketones and therefore can be removed. The present invention has been attained on the basis of the discovery, and the object thereof is to propose a method of purifying a macrocyclic ketone of high purity which is not colored and has no bad odor and which has an excellent quality for use as perfumes and the like, by a simple operation with high efficiency.

The subject matter of the present invention resides in the means for overcoming the above-mentioned problems, and the first embodiment of the invention comprises light-irradiation of a macrocyclic diketone containing macrocyclic ketone and the second embodiment thereof comprises the said light-irradiation followed by treatment of the resulting macrocyclic ketone with an active charcoal.

DETAILED DESCRIPTION OF THE INVENTION

Figure 1:
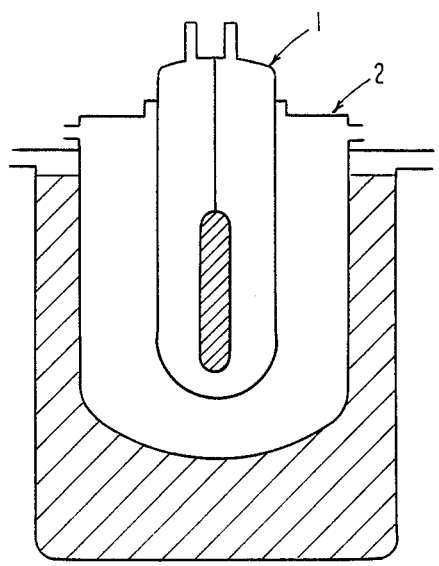
FIG. 1 shows a sectional view of the container for light-irradiation used in Examples 9 to 12 of the invention.

Specifically, the present invention is noticeably effective when applied to a macrocyclic ketone obtained by cyclization of a diester of a straight chain alkanedicarboxylic acid having from 9 to 18 carbon atoms by acyloin condensation followed by reduction of the resulting intermediate.

Various methods have heretofore been known for preparing the macrocyclic ketones as herein referred to by the present invention, and one example of the methods is mentioned below.

First, a straight chain alkanedicarboxylic acid is heated together with a lower alcohol in the presence of an acid catalyst under reflux for esterification. Next, a solution of the diester of the straight chain alkanedicarboxylic acid as dissolved in an organic solvent is dropwise added to a suspension formed by suspending at least one of alkali metals, alkaline earth metals and the mercury amalgams thereof in an organic solvent and kept at room temperature to 140° C, for acyloin condensation.

After completion of the acyloin condensation, the resulting reaction solution is cooled and neutralized with an aqueous solution of acetic acid, sulfuric acid or hydrochloric acid, and then the aqueous layer is separated and removed, and the acyloin condensation product is obtained by distillation. The acyloin condensation product is thereafter reduced with zinc powder and hydrochloric acid in an organic solvent, and the resulting product is isolated by distillation under reduced pressure to obtain a macrocyclic ketone. The thus obtained macrocyclic ketone is colored in yellow as containing a diketone as an impurity.

The macrocyclic ketone is purified by light-irradiation. The macrocyclic ketones that can be used are those partially purified by distillation under reduced pressure or recrystallization. Further, it is needless to say that the present invention can also be applied to a macrocyclic ketone which has been stored for a long period of time so that a part thereof has been changed to a macrocyclic diketone by oxidation or the like to be colored, to have the same effect thereon.

For the light-irradiation, the light to be used may anyone from visible ray and ultraviolet ray, and therefore sun light, fluorescent lamp, UV lamp, xenon lamp, indium lamp, metal halide lamp and the like can be used as a light source.

In the practice of the present invention, the strength of the light to be irradiated and the irradiation time can properly be determined in consideration of the degree of the purity of the macrocyclic ketone to be treated, or that is, the amount of the macrocyclic diketone in the macrocylclic ketone, etc. However, too strong irradiation for a long period of time is unfavorable as causing deterioration of the macrocyclic ketone.

For the light-irradiation, the macrocylic ketone can be processed as a solid or, alternatively, this can be processed in the form of a melted state or a solution as dissolved in an organic solvent such as a lower alcohol or the like. In particular, alcohols such as methyl alcohol, ethyl alcohol or the like are preferably used as the solvent, since the difference in the temperature-dependent solubility of the macrocyclic ketone in the solvent is noticeable and the recovery loss in recrystallization is small. In this case, it is preferred that the concentration of the macrocyclic ketone in the solution is as high as possible, since the removal of the solvent in the subsequent step is easy.

After light-irradiation, the decomposition product or polymerized product of the macrocyclic diketone can be removed by distillation or recrystallization. For easy and complete removal of the product, it is preferred to use an active charcoal. Although the active charcoal treatment can be effected by any method with fixed bed, fluidized bed or the like, it is sufficient merely to add an active charcoal to the macrocyclic ketone-containing solution in an amount of 1 to 10 wt% or so, after the above-mentioned light-irradiation of the solution, and to stir and filtrate the resulting mixture.

The macrocyclic ketone thus purified by the above-mentioned method is stored and sold in the state as sealed up and shielded from light so as to prevent oxidation or decomposition of the ketone.

The following examples and comparative examples are intended to concretely demonstrate the effect of the present invention but not to limit the scope thereof in any way.

EXAMPLES 1 TO 4

In a 10 liter-volume Herz flask was charged 4 liters of dry xylene, and 39.8 g of sodium was added thereto. The mixture was kept at 105° C in a nitrogen atmosphere. Next, a solution of 110 g of dimethyl n-pentadecanedioate in 250 ml of xylene was added dropwise to the mixture over a period of 6 hours.

The resulting mixture was cooled with ice, and 150 ml of glacial acetic acid was added to the reaction mixture for neutralization. After the aqueous layer was separated, the organic layer was distilled under reduced pressure and the fraction at 152 to 166° C (0.33 to 0.95 mmHg) was collected to obtain 65.0 g of the acyloin condensation product.

30 g of the thus obtained 2-hydroxycyclopentadecanone was dissolved in 250 ml of xylene solvent, 30 g of zinc powder was dispersed therein and 200 ml of concentrated hydrochloric acid was added dropwise thereto over a period of 2 hours for reduction. After completion of the reaction, the reaction solution was filtered to remove the zinc powder. The resulting reaction solution was washed with water and 10 g of anhydrous magnesium sulfate was added thereto for drying. After filtration, the solvent was distilled away by evaporation to obtain 28 g of the reaction product. 10 g of the reaction product was put in a Herz flask and melted under heat with an oil bath. A capillary was inserted into the flask and the internal pressure of the flask was reduced with a vacuum pump. Then the content in the flask was distilled under the condition of an absolute pressure of 3 mm Hg and a temperature of 142 to 144° C to obtain cyclopentadecanone which is a macrocyclic ketone as a fraction distilled. The cyclopentadecanone was colored in yellow and had an irritant odor, and the musky smell thereof was weak. As a result of analysis of the cyclopentadecanone with gas chromatography, cyclopentadecanedione was found in an amount of 0.1 wt%.

Next, the solid cyclopentadecanone was put in a sample bottle having a diameter of 26 mm, a height of 45 mm and a volume of 20 ml and was irradiated with sun light, or was put in a test tube having a diameter of 23 mm and a height of 199 mm and was irradiated with a 30 W fluorescent lamp. In both cases, the irradiation was effected until the yellow color of the solid could no more be observed with the naked eye. On the other hand, the cyclopentadecanone was dissolved in ethyl alcohol to form a solution having a 20 wt% concentration, and the solution was also put in the same containers and irradiated to light in the same manner. As to the results obtained in these cases, the time required for discoloration is shown in Table 1 below. The thus light-irradiated solids were subjected to a test for the fragrance thereof as these were and, as a result, these had no irritant odor.

The cyclopentadecanone was analyzed by gas chromatography and, as a result, no cyclopentadecanedione was detected. The purity of the cyclopentadecanone was 96.9%.

On the other hand, active charcoal was added to the light-irradiated cyclopentadecanone-containing solutions in an amount of 5 wt% on the basis of the cyclopentadecanone in the solution and stirred for 20 minutes at room temperature. Afterwards, the active charcoal was removed by filtration and the solvent was also removed. The thus purified cyclopentadecanone was subjected to the test for the fragrance thereof and, as a result, this had no irritant odor. The cyclopentadecanone was also analyzed by gas chromatography in the same manner as mentioned above and, as a result, no cyclopentadecanedione was detected. The purity of the cyclopentadecanone was 98.2%.

TABLE 1

| Example No. | State | Light Source | Time (hr) |
| --- | --- | --- | --- |
| Example 1 | Solid | Sun Light | 9.25 |
| Example 2 | Solid | Fluorescent Light | 282.31 |
| Example 3 | Solution | Sun Light | 2.75 |
| Example 4 | Solution | Fluorescent Light | 210.13 |

EXAMPLES 5 TO 8

The cyclopentadecanone obtained by the same method described in the above-mentioned Examples 1 to 4 was recrystallized from ethyl alcohol and then distilled under the condition of an absolute pressure of 3 mmHg and a temperature of 142 to 144° C and again recrystallized from ethyl alcohol.

Although the cyclopentadecanone was almost free from irritant odor, this was colored in pale yellow. As a result of analysis of the cyclopentadecanone by gas chromatography, cyclopentadecanedione was found in an amount of 0.01 wt%.

This was irradiated with light in the same manner as in Examples 1 to 4. The results obtained are shown in Table 2 below. As a result of a test for the fragrance of the product, the product had no irritant odor in every sample; and as a result of analysis by gas chromatography, no cyclopentadecanedione was detected.

TABLE 2

| Example No. | State | Light Source | Time (hr) |
| --- | --- | --- | --- |
| Example 5 | Solid | Sun Light | 0.10 |
| Example 6 | Solid | Fluorescent Light | 3.00 |
| Example 7 | Solution | Sun Light | 0.10 |
| Example 8 | Solution | Fluorescent Light | 3.00 |

EXAMPLES 9 TO 12

The cyclopentadecanone obtained by the same method as described in Examples 1 to 4 was dissolved in methyl alcohol to form a 47.4 wt% solution.

2.2 liters of the resulting solution was put in a 2.6 liter-volume container having a 400 W indium lamp (1)

(HI400PL by Toshiba Co., Ltd., main wavelength 451 nm) in the inside thereof and a cooling jacket (2) therearound as shown in FIG. 1, and this was irradiated to light under the condition as indicated in Table 3 below until the yellow color of the solution could no more be observed. As to the results, the time required for discoloration is shown in Table 3. As a result of a test for the fragrance of the product, the product had no irritant odor in every sample; and as a result of analysis by gas chromatography, no cyclopentadecanedione was detected.

TABLE 3

| Example No. | Condition | Time (hr) |
| --- | --- | --- |
| Example 9 | Stirring with stirrer | 5.5 |
| Example 10 | Container was covered with aluminium foil for light-shielding, with stirring with stirrer. | 1.2 |
| Example 11 | Container was covered with aluminium foil for light-shielding, with stirring by $N_2$ gas-bubbling. | 1.0 |
| Example 12 | Container was covered with aluminium foil for light-shielding, with stirring by air-bubbling. | 1.0 |

EXAMPLE 13

The same cyclopentadecanone-containing methyl alcohol solution as described in Examples 9 to 12 was put in a laboratory dish (inner diameter: 204 mm, height: 45 mm) in an amount of 1.5 liters, the dish being covered with an aluminium foil except the top thereof for light-shielding. From the top of the container, the solution therein was irradiated with a light of a 400 W metal halide lamp (Sun Light Lamp DR400/T, by Toshiba Co., Ltd., main wavelength 545 nm) with stirring with a stirrer, the distance from the solution surface to the lamp being 800 mm, until the yellow color of the solution could no more be observed. The time required for the discoloration was 2.25 hours.

As mentioned in detail in the above, a macrocyclic diketone-containing macrocyclic ketone is purified by irradiation of light thereto in accordance with the method of the present invention so that a purified macrocyclic ketone which is not colored and has no bad odor and which is excellent in the quality as perfumes and the like can be obtained by a simple operation with high efficiency. Preferably, the thus light-irradiated macrocyclic ketone may be treated with an active charcoal so that a macrocyclic ketone with a higher quality can be obtained. Thus the present invention is characterized by the particular effect.

While the invention has been described in detail and with reference to specific embodiments thereof, it will be apparent to one skilled in the art that various changes and modifications can be made therein without departing from the spirit and scope thereof.

What is claimed is:

1. A method for purifying a macrocyclic ketone which comprises light-irradiating a macrocyclic ketone containing a macrocyclic diketone as an impurity, wherein said ketone is obtained by the cyclization of a diester of a straight alkanedicarboxylic acid having from 9 to 18 carbon atoms by acyloin condensation, followed by reduction of the resulting intermediate, whereby purified macrocyclic ketone is obtained therefrom.

2. A method for purifying a macrocyclic ketone which comprises light-irradiating an alcohol solution of a macrocyclic ketone containing a macrocyclic diketone as an impurity, wherein said ketone is obtained by the cyclization of a diester of a straight alkanedicarboxylic acid having from 9 to 18 carbon atoms by acyloin condensation, followed by reduction of the resulting intermediate, whereby purified macrocyclic ketone is obtained therefrom.

3. A method for purifying a macrocyclic ketone as in claim 1, wherein the macrocyclic ketone is cyclopentadecanone.

4. A method for purifying a macrocyclic ketone as in claim 1, wherein the light-irradiation is conducted with a light source selected from the group consisting of sun light, fluorescent lamp, UV lamp, xenon lamp, indium lamp and metal halide lamp.

5. A method for purifying a macrocyclic ketone which comprises a light-irradiating a macrocyclic ketone containing a macrocyclic diketone as an impurity, wherein said ketone is obtained by the cyclization of a diester of a straight alkanedicarboxylic acid having from 9 to 18 carbon atoms by acyloin condensation, followed by reduction of the resulting intermediate, and treating the resulting intermediate with an active charcoal, whereby purified macrocyclic ketone is obtained therefrom.

6. A method for purifying a macrocyclic ketone as in claim 5, wherein the light-irradiation is conducted with a light source selected from the group consisting of sun light, fluorescent lamp, UV lamp, xenon lamp, indium lamp and metal halide lamp.

* * * * *